US00PP08068P

United States Patent [19]

Gerawan

[11] Patent Number: Plant 8,068

[45] Date of Patent: Dec. 22, 1992

[54] PRIMA BLACK PLUM 8-15

[76] Inventor: Michael R. Gerawan, 6407 S. Engelhart, Reedley, Calif. 93654

[21] Appl. No.: 633,317

[22] Filed: Dec. 24, 1990

[51] Int. Cl.[5] ..... A01H 5/00

[52] U.S. Cl. ..... Plt./38.1

[58] Field of Search ..... Plt./38

*Primary Examiner*—James R. Feyrer

*Attorney, Agent, or Firm*—Worrel & Worrel

[57] ABSTRACT

A new and distinct variety of plum tree producing fruit of catawba coloration which are mature for harvesting and shipment approximately the first week in August in the San Joaquin Valley of central California approximately two weeks after "Friar" plum tree and which have a mild, subacid taste with a pronounced pistil point and good shipping and handling characteristics.

1 Drawing Sheet

BACKGROUND OF THE NEW VARIETY

The present invention relates to a new and distinct variety of plum tree, hereinafter be denominated varietally as the "Prima Black Plum 8-15" plum tree, and more particularly to a plum tree which produces freestone fruit having a distinctive catawba coloration with flesh of a nankeen coloration with a mild subacid flavor, the fruit having a pronounced pistil point and being mature for harvesting and shipment approximately the first week of August in the San Joaquin Valley of central California.

There are a variety of attributes which tree fruit may possess which may distinguish the variety from other tree fruit in the marketplace. Commerical success is often dependent upon somewhat subtle distinctions. While ripening data is one of the more important considerations, within a given ripening period a host of rather subtle distinctions may prove important. While it might seem that only flavor would be of any concern, this is not in fact the case. Size, shape, texture, aroma and shelf lift may all be of significance. Similarly, the skin and flesh coloration may afford an appeal, or, conversely, a detraction such as to be controlling to significant segments of the purchasing public. In this regard, personal preference plays a substantial role in the equation. More technical considerations such as keeping quality, resistance to disease, shipping and handling quality and the like may control which varieties are selected for planting by the grower.

The new variety of the present invention possesses a number of attributes which caused it to be selected for further development and which are believed to indicate a promising commercial life. The fruit of the "Prima Black Plum 8-15" plum tree is freestone and of large size averaging between 66 mm and 71 mm in diameter. The fruit exhibits a distinctively pronounced pistil point and has a particularly attractive coloration. The skin coloration is catawba and the flesh is nankeen, the contrast being particularly attractive. The fruit ripens for harvest about two weeks after the "Friar" plum tree, or about the first week of August in the San Joaquin Valley of central California.

ORIGIN AND ASEXUAL REPRODUCTION OF THE NEW VARIETY

The present variety of plum tree hereof was discovered in 1984 by the inventor as an open pollinated seedling in a cultivated area on the inventor's property Ranch 33 in Sanger in the San Joaquin Valley of central California. The new variety was selected as the result of a mass breeding program. The seedling was selected from this program, but its parentage is unknown. Seeds collected for the mass breeding program came from several ranches encompassing nearly five thousand acres growing many varieties of tree fruit. No effort was made to retain the specific pedigree of any particular seed lot. The inventor asexually reproduced the new variety by grafting and budding test trees on the same property. The test trees have been observed through several growing seasons and the inventor has witnessed that the progeny have characteristics identical to those observed in the parent.

SUMMARY OF THE NEW VARIETY

The "Prima Black Plum 8-15" plum tree is characterized as to novelty by producing freestone fruit which are symmetrical in form being globose to slightly oblate with a pronounced pistil point. The fruit of the new variety is of large size averaging from 66 mm to 71 mm in diameter and has a distinctive skin coloration of catawba with a flesh of nankeen and is ripe for commercial harvesting and shipment approximately the first week in August in the San Joaquin Valley of central California.

BRIEF DESCRIPTION OF THE DRAWING

The accompanying drawing is a photograph showing the plum tree of the new variety including fruit of the new variety sectioned one with the stone removed to expose the pit cavity and the other with the stone left in place; a second in top plan view showing the apex end thereof; a third in side elevation showing the pronounced pistil point thereof; a fourth in bottom plan view to show the base thereof; and a fifth in top plan view with its natural waxy coating left in place; and representative foliage of the new variety.

DETAILED DESCRIPTION

Referring more specifically to the pomological details of this new and distinct variety of plum tree, the following has been observed under the ecological conditions prevailing at a ranch which is located in Sanger, Calif. All major color code designations are by reference to the Dictionary of Color, by Maerz and Paul, First Edition, 1930. Common color names are also employed occasionally.

TREE

Generally:
- *Size.*—Medium.
- *Figure.*—Upright. The subject variety is upright to upright-spreading in form. The asexually reproduced trees were pruned in a standard vase-shaped configuration.
- *Productivity.*—Productive.
- *Regularity of bearing.*—Regular.

Trunk:
- *Size.*—Stocky.
- *Surface texture.*—Medium shaggy.

Branches:
- *Size.*—Medium.
- *Surface texture.*—Medium shaggy.
- *Color.*—Base — Page 39, Plate 8 C-11 Bark Mocha+. Streak Color - Page 33, Plate 5, B-11, Cocoa Br.
- *Lenticels.*—Numerous.
- *Size.*—1 mm (0.04 inches) by 3 mm (0.12 inches) by 6 mm (0.24 inches).

LEAVES

Size:
- *Generally.*—Medium.
- *Average length.*—97 mm (3.88 inches) to 102 mm (4.08 inches).
- *Average width.*—38 mm (1.52 inches) to 43 mm (1.72 inches).

Form: Ovate.

Color:
- *Upwardly disposed surface.*—Page 71, Plate 24, L-1, Yew Green.
- *Downwardly disposed surface.*—Page 67, Plate 22, B-5, Mistletoe.

Marginal form: Double serrate.

Glandular characteristics: 1 to 3, globose, opposite and alternate.

Petiole:
- *Length.*—15 mm (0.6 inches) to 17 mm (0.68 inches).
- *Thickness.*—2 mm (0.08 inches).

Stem glands:
- *Number.*—From none to two.
- *Arrangement.*—Alternate and opposite.
- *Type.*—Globose.
- *Size.*—Small.
- *Color.*—Green.

Stipules: Leaf stipules present, two per leaf occurring at the base of the petiole. Stipules relatively long and lanceolate in form.

Leaf glands: One to three on base of leaf margin. In addition, glands can occur on the petiole, variable in number from none to two.

FLOWERS

The following description was prepared from bloom taken from trees of the subject variety growing in a test planting near Sanger, Calif. in early March, 1992. The number of chilling hours below 45 degrees Fahrenheit in this fruit growing area of Fresno County, Calif. in the 1991-1992 winter season was nearly 1200 hours. This represents an above average accumulation of cold hours for this location in 1992.

Flower buds:
- *Size.*—medium, conic in form, plump and slightly appressed to the stem. The buds are hardy under typical climatic conditions in the San Joaquin Valley of California.
- *Surface texture.*—Very slightly pubescent.
- *Scales.*—Color — Coromandel Brown (7-L-11).
- *Shape.*—Obtuse.

Pedicle: Medium.

Stamens: Numerous.

Pistil: One.

Date of bloom: Slightly past mid-season, about with the "Wickson" plum tree. The date of bloom is approximately medium in timing in relation to other standard plum varieties and approximately simultaneous with the "Santa Rose", "El Dorado" and "Wickson" plum trees. In 1992 the first bloom was February 25 and full bloom March 2. No pollination tests have been conducted, but it is believed the new variety requires pollination as in conventional varieties. This is achieved by proximity to other varieties blooming at the same time such as the "Santa Rose", "El Dorado" and "Wickson" plum trees.

Flower:
- *Size.*—Medium.
- *Diameter.*—Fully expanded averages from 14 mm (0.5511 inches) to 15 mm (0.5905 inches). At full maturity the flowers are slightly cupped inwards.

Bloom:
- *Quantity.*—Very Abundant.

Flower buds:
- *Number.*—Varies from 6 to 10 per node.

Petals:
- *Number.*—Five.
- *Size.*—Medium.
- *Length.*—Averaging from 9 mm (0.3543 inches) to 10 mm (0.3937 inches).
- *Width.*—6 mm (0.2362 inches) to 7 mm (0.2755 inches).
- *Shape.*—Variable from ovate to oval in form.
- *Color.*—White (1-A-1).

Petal claw:
- *Form.*—Truncate and short.

Petal margins: Moderately undulate.

Petal Apices: Variable but most often obtuse.

Pedicel: Moderately long from 15 mm (0.5905 inches) to 16 mm (0.6299 inches).
- *Thickness.*—Average 1.0 mm (0.0393 inches).
- *Color.*—Light green 18-I-4).

Pedicel surface: Glabrous.

Calyx:
- *Surface.*—Glabrous.
- *Color.*—Light green (19-J-3).

Nectaries:
- *Color.*—Brownish-green (Cloudy Amber 12-K-3). Nectaries darken wtih age to (12-K-5).

Anthers:
- *Size.*—Medium.
- *Color.*—Golden yellow (Golden Glow 9-L-6) both dorsally and ventrally.

Pollen: Moderately abundant.
- *Color.*—Yellow (Sunflower yellow 9-L-4).

Stamens:
- *Length.*—Variable. Stamens equal to slightly longer in length than the pistil. From 7 mm (0.2755 inches) to 8 mm (0.3149 inches).
- *Color.*—White (1-A-1).

Pistil:
*Surface.*—Glabrous.
*Length.*—From 8 mm (0.3149 inches) to 9 mm (0.3543 inches).
*Color.*—Light green (17-G-2).

FRUIT

Maturity when described: Ripe for commercial harvesting and shipment approximately the first week of August near Sanger, Calif., about two weeks after the "Friar" plum tree. The new variety requires thinning as with other varieties of plum trees.

Size:
*Average diameter.*—66 mm (2.64 inches) to 71 mm (2.84 inches).
*Average diameter transverse in the suture plane.*—65 mm (2.6 inches) to 70 mm (2.8 inches).
*Average diameter transverse and at right angles to the suture plane.*—63 mm (2.52 inches) to 66 mm (2.64 inches).

Form:
*Uniformity.*—Uniform.
*Symmerical.*—Globose to slightly oblate with pronounced pistil point.

Suture:
*Generally.*—Distinct line, slightly depressed.
*Length.*—95 mm (3.8 inches) to 100 mm (4 inches).

Ventral surface:
*Generally.*—Smooth.

Stem cavity:
*Generally.*—Obtuse.
*Depth.*—15 mm (0.6 inches) by 25 mm (1.0 inches) by 10 mm (0.4 inches).

Stem:
*Caliper.*—3 mm (0.12 inches).
*Caliper — length.*—10 mm (0.4 inches).

Apex:
*Shape.*—Rounded.

Base: Flat.

Pistil point: Pronounced, 3 mm (0.12 inches) to 5 mm (0.2 inches) in length.

Skin:
*Thickness.*—Medium.
*Texture.*—Medium.
*Tendency to crack.*—None.
*Color.*—Page 135, Plate 56, J-10, Catawba.
*Pubescence.*—None.

Flesh:
*Color.*—Page 43, Plate 10, F3, Nankeen.
*Surface of pit cavity.*—Smooth.

*Color of pit well.*—Same as flesh.
*Amygdalin.*—None.
*Juice production.*—Juicy.
*Flavor.*—Subacid, mild. The fruit of the subject variety is sweet with moderate acidity and a mild flavor.
*Aroma.*—None.
*Texture.*—Tender.
*Fibers.*—Moderate.
*Ripening.*—Even.
*Eating quality.*—Good.

Stone:
*Attachment.*—Freestone.
*Fibers.*—None.
*Size.*—Length — 26 mm (1.04 inches.)
*Width.* —19 mm (0.76 inches).
*Thickness.*—10 mm (0.4 inches).
*Form.*—Generally — Oval.
*Color.*—Page 43, Plate 10, I-b 9, Jacinthe.
*Base.*—Shape — Flat.
*Sides.*—Fairly smooth.
*Ridges.*—A few near base, rounded.
*Grooves.*—None.
*Dorsal edge.*—Narrow with slight groove near middle.
*Ventral edge.*—Slight wing from middle to apex.
*Tendency to split.*—None.

Use: Fresh.

Keeping quality: Good.

Shipping and Handling Qualities: good.

Although the new variety of plum tree possesses the described characteristics noted above as a result of the growing conditions prevailing near Sanger in the central San Joaquin Valley of California, it is to be understood that variations of the usual magnitude and characteristics incident to changes in growing conditions, fertilization, irrigation, pruning and pest control are to be expected.

Having thus described and illustrated my new variety of plum tree, what I claim as new and desire to be secured by Plant Letters Patent is:

1. A new and distinct variety of plum tree substantially as illustrated and described and which produces freestone fruit of a catawba coloration with a very pronounced pistil point which are mature for commercial harvesting and shipment approximately the first week of August in the San Joaquin Valley of central California about or two weeks after the "Friar" plum tree.

* * * * *

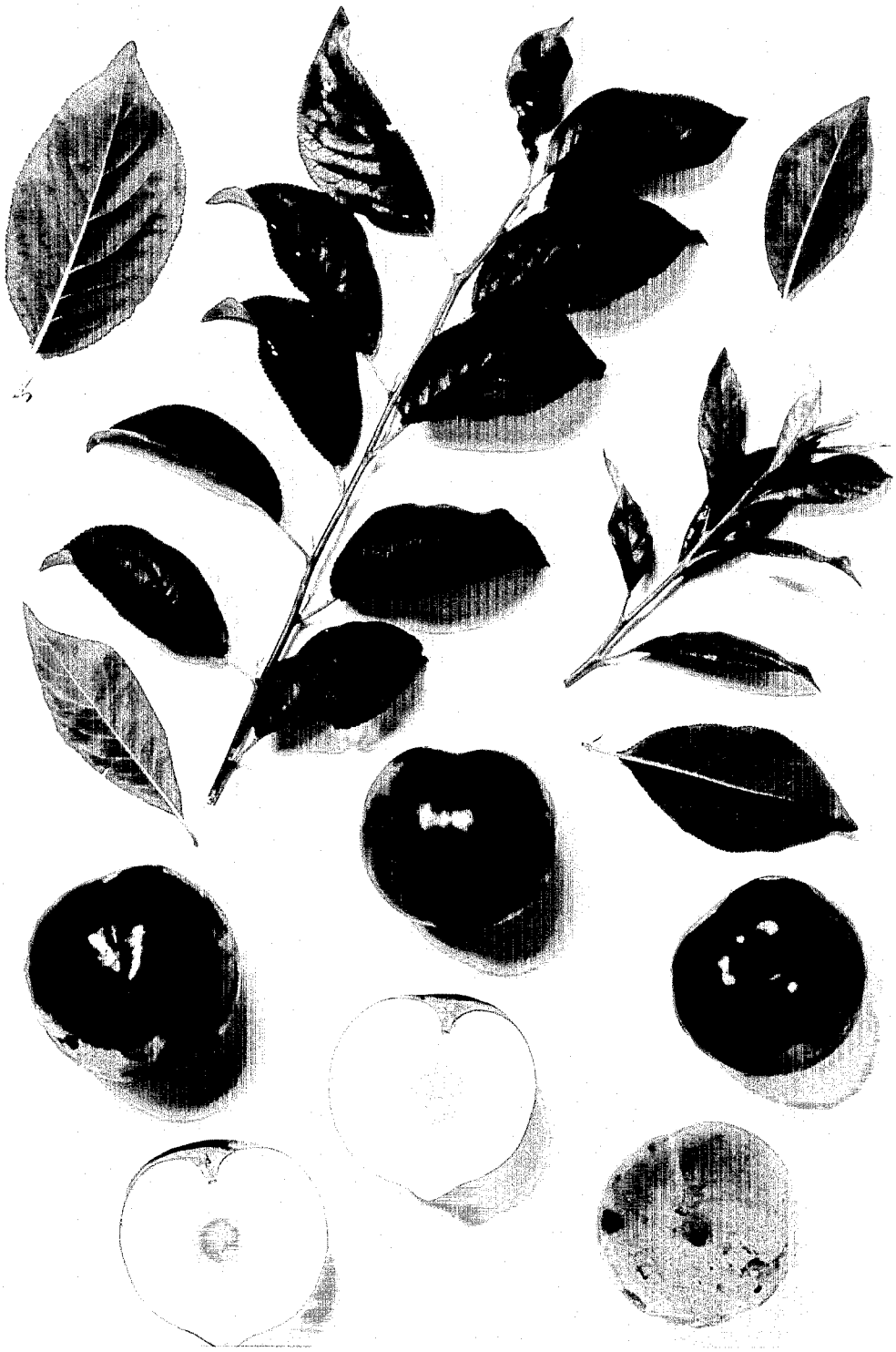

UNITED STATES PATENT AND TRADEMARK OFFICE

CERTIFICATE OF CORRECTION

PATENT NO. : Plant 8,068

DATED : December 22, 1992

INVENTOR(S) : Michael R. Gerawan

It is certified that error appears in the above-identified patent and that said Letters Patent is hereby corrected as shown below:

Column 1, Line 22, delete "lift" and substitute ---life---.

Column 4, Line 8, after "Obtuse." insert

---Flowers-Generally-Small---

Column 4, Line 18, between "bloom" and "March" insert

---was---.

Column 5, Line 23, delete "Symmerical" and substitute

---Symmetrical---.

Signed and Sealed this

Nineteenth Day of October, 1993

Bruce Lehman

*Attest:*

BRUCE LEHMAN

*Attesting Officer*

*Commissioner of Patents and Trademarks*